US000001439H

United States Statutory Invention Registration [19]

[11] Reg. Number: H1439

Hairston

[43] Published: May 2, 1995

[54] METHOD TO INCREASE THE LEVEL OF α-GLYCOL IN LIQUID EPOXY RESIN

[75] Inventor: Thomas J. Hairston, Lake Jackson, Tex.

[73] Assignee: The Dow Chemical Company, Midland, Mich.

[21] Appl. No.: 138,661

[22] Filed: Oct. 18, 1993

[51] Int. Cl.[6] ..... C08F 283/00; C08G 59/00; C07D 301/27

[52] U.S. Cl. ..... 525/523; 528/87; 528/499; 549/517

[58] Field of Search ..... 549/517; 525/523; 528/87, 499

[56] References Cited

U.S. PATENT DOCUMENTS 4,358,577 11/1982 McCrary et al. ..... 525/507

*Primary Examiner*—Shean Wu

*Attorney, Agent, or Firm*—Charles J. Maurer, III; Philip D. Shepherd; Richard G. Waterman

[57] ABSTRACT

The performance of epoxy resins in several end-uses is enhanced by the presence of small quantities of hydrolyzed resin terminated by α-glycol groups. The invention is a process in which a mixture that contains liquid epoxy resin and water is reacted at elevated temperatures in order to hydrolyze epoxy groups into α-glycol groups, characterized in that: (1) the reaction temperature is between 130° C. and 200° C; (2) the reaction mixture contains 0.5 and 10 parts water per 100 parts resin by weight; and (3) the mixture contains 0 to 1 weight percent organic solvents and 0 to 100 ppm each of: organic acids, organic diacids, phosphonium compounds, and alkali or alkaline earth metals and their salts. The process raises the level of α-glycol groups in the resin, but uses no solvents or catalysts, so that it is easy to clean up the resulting resin.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD TO INCREASE THE LEVEL OF α-GLYCOL IN LIQUID EPOXY RESIN

BACKGROUND OF THE INVENTION

The present invention relates to the art of making epoxy resins.

Liquid epoxy resin is usually made by reacting a dihydric phenol, such as bisphenol A, with excess epihalohydrin in the presence of an alkali metal hydroxide, such as sodium hydroxide. Unused epihalohydrin and catalyst are usually recycled back into the reaction. See, for instance, Wang et al, U.S. Pat. No. 4,499,255 (Feb. 12, 1985) and Massingill, U.S. Pat. No. 4,313,886 (Feb. 2, 1982). The resulting resin usually contains predominantly the diglycidyl ether of the dihydric phenol, with minor quantities of oligomer and or resin that is terminated by α-glycol groups.

The dihydric phenol and the diglycidyl ether are preferably represented by Formula 1:

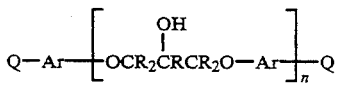

(1)

wherein:

Ar represents an aromatic group.

Each Q is a hydroxyl group in the dihydric phenol, and Q is a glycidyl ether moiety represented by Formula ( 2 ):

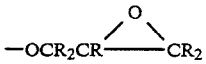

(2)

in the epoxy resin.

Each R represents a hydrogen atom, a halogen or a lower alkyl group.

"n" represents a number of repeating units. "n" is usually 0.1 to 0.2 in liquid epoxy resin.

Usually, a small percentage of the glycidyl ether moieties (Q) are hydrolyzed during this process to make α-glycol groups, which are preferably represented by Formula (3):

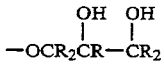

(3)

For many uses, it is desirable for the resin to contain only a very small amount of α-glycol. First, resins that contain more than about 2 percent α-glycol are difficult to wash after they are made because they form emulsions when impurities are washed from the resin using water. Second, resins that contain very low levels of α-glycol have superior performance properties for many applications, such as high glass-transition temperature in electrical laminates. Therefore, it is frequently desirable to manufacture liquid epoxy resin that contains very low levels of α-glycol. This can easily be done by removing hydrolysis products of epihalohydrin from recycled epihalohydrin before returning the epihalohydrin to the reaction vessel.

On the other hand, somewhat higher levels of mono-α-glycol-containing resin (in which one Q is a glycidyl ether moiety of Formula (2) and the other Q is an α-glycol of Formula (3)) are frequently desirable for several applications. Small amounts of mono-α-glycol resin greatly accelerate the curing of liquid epoxy resin with amine catalyst. Furthermore, resins that contain moderate amounts of mono-α-glycol resin interact better with thixotropic agents and flow modifiers. Therefore, it is desirable to increase the levels of mono-α-glycol resin in liquid epoxy resins that contain very little α-glycol, for some uses. However, bis-α-glycol resin (in which both Q are α-glycol moieties of Formula (3)) are undesirable and are preferably minimized.

It has been known in the prior art to make hydrolyzed epoxy resins that can be added to nonhydrolyzed resin to make a mixture containing desired amounts of α-glycol. For instance, Walker, U.S. Pat. No. 3,632,836 describes the hydrolysis of epoxy resins in a dilute aqueous solution with an acidic catalyst at a temperature of 50° C. to 374° C. Cavitt, U.S. Pat. No. 4,404,335 (Sep. 13, 1983) teaches to hydrolyze epoxy resins without an organic solvent using a catalyst that contains a dicarboxylic acid (such as oxalic acid) and a phosphonium compound.

The know processes have draw backs which make them undesirable for use in mass producing large quantities of liquid epoxy resin that contain moderate α-glycol content. First, they use catalysts and sometimes solvents that must be removed from the resin before it can be sold or used. Second, they make large quantities of bis-α-glycol species resin in addition to the mono-α-glycol resin.

What is needed is a process to moderately increase the level of mono-α-glycol resin in an epoxy resin to a desired level without the need for a catalyst or solvent.

SUMMARY OF THE INVENTION

The present invention is a process in which a mixture of liquid epoxy resin and water is reacted at elevated temperatures in order to hydrolyze epoxy groups into α-glycol groups, characterized in that:

(1) the reaction temperature is between 130° C. and 200° C.;

(2) the reaction mixture contains between 0.5 and 10 parts water per 100 parts resin by weight; and (3) the mixture contains 0 to 1 weight percent organic solvents and 0 to 100 ppm each of: organic acids, organic diacids, phosphonium compounds, and alkali or alkaline earth metals and their salts.

The parts and percentages are preferably measured by high performance liquid chromatography as described in Example 1.

The process has several advantages over the prior art. It can be run either in a batch fashion or continuously. It can easily make liquid epoxy resin that contains commercially desirable levels of mono-α-glycol resin. It makes little or no bis-α-glycol resin. It uses no catalyst, so only water needs to be separated at the completion of the reaction. The resin can be used for ordinary thermoset uses, such as adhesives and coatings.

DETAILED DESCRIPTION OF THE INVENTION

The present invention uses a liquid epoxy resin. Suitable resins and processes to make them are described previously. The non-oligomerized resin contains an aromatic group (Ar) linking two glycidyl ether moieties (Q), as illustrated in Formula 1. The aromatic group contains an aromatic ring or a moiety containing two fused or unfused aromatic rings. The aromatic rings are preferably carbocyclic. They may have substituents that do not interfere with the manufacture or use of the resin, such as lower ($C_1$ to $C_6$) alkyl groups, halogen atoms, alkoxy groups and the like, but they are preferably unsubstituted. Unfused rings may be linked by a bond or by a divalent moiety that does not interfere with the manufacture or use of the resin. Examples of divalent moieties include an oxygen atom, a lower hydrocarbyl group, a halogenated lower hydrocarbyl group, a ketone group, a fluorene group and the like. The hydrocarbyl groups are preferably alkylene groups. The divalent moiety is preferably a methylene or isopropylene moiety, and is most preferably isopropylene. Each Ar is most preferably a 2,2-bis-(p-phenylene)-isopropylidene moiety, which optionally contains methyl or halogen substituents bonded to the phenylene rings.

Each R in Formulae 1, 2, and 3 is preferably hydrogen.

As previously explained, the liquid epoxy resin usually contains small quantities of oligomer and α-glycol-containing resins at the commencement of the reaction. The liquid epoxy resin preferably contains 70 to 100 weight percent diglycidyl ether of the dihydric phenol, more preferably 80 to 90 weight percent, and most preferably about 85 weight percent. The liquid epoxy resin preferably contains 0 to 30 weight percent oligomer, more preferably 10 to 20 weight percent oligomer, and most preferably about 15 weight percent oligomer. The oligomers are preferably represented by Formula 1, wherein "n" is 0 or greater. The average "n" is preferably 0 to 0.2, more preferably 0.10 to 0.15 and most preferably about 0.12.

The process can use resins that contain low, moderate or high levels of α-glycol, but it is most useful with resins that contain relatively little α-glycol. The starting liquid epoxy resin preferably contains 0 to 2 weight percent α-glycol-containing species, more preferably 0 to 1 weight percent α-glycol-containing species, and most preferably 0 to 0.5 weight percent α-glycol-containing species. The quantity of α-glycol in the resin is preferably no more than 1 equivalent percent the quantity of glycidyl ether moieties, more preferably no more than 0.5 equivalent percent, and most preferably, no more than 0.3 equivalent percent.

It is possible that the liquid epoxy resin may contain small quantities of impurities from previous steps. Some impurities can promote cross-linking during the hydrolysis, such as epihalohydrins, acids, and alkali and alkaline earth metals and their salts. These impurities should be rigorously excluded. The liquid epoxy resin preferably contains less than 100 ppm of those impurities, more preferably less than 50 ppm, more highly preferably less than 25 ppm and most preferably less than about 10 ppm. For instance, the liquid epoxy resin preferably contains no more than 5 ppm sodium, 6 ppm inorganic chloride and 10 ppm epichlorohydrin. Optimally, the liquid epoxy resin contains 0 ppm of those impurities.

Other impurities, such as common organic solvents, do not promote cross-linking to the same extent. Although these impurities are not desirable, they do not need to be excluded as rigorously. Examples of common solvents that fall into this category include aromatic and polar organic solvents that are liquid at about 25° C. such as toluene, xylene, alkyl ketones, glycols, ethers and glycol ethers, alcohols and the like. The liquid epoxy resin preferably contains no more than about 1 weight percent of those impurities, more preferably no more than about 0.5 weight percent and most preferably no more than about 0.1 weight percent.

Preferred resins are commercially available from The Dow Chemical Company under the trademark D.E.R.* 330 and D.E.R.* 383. They can also be made by the processes described previously. (*- trademark of The Dow Chemical Company)

The reaction temperature is preferably at least 145° C. and more preferably at least 165° C. The reaction temperature is preferably no more than 180° C. and more preferably no more than 175° C. The resin is contacted with water either before, during or after it has been heated. The resin is preferably heated to reaction temperature before it is contacted with the water.

It is not critical whether the water is added to the reaction vessel as liquid water or as steam. The water is preferably added as steam. The ratio of water to resin is preferably at least 0.5 phr water, more preferably at least 1 phr water and most preferably at least 2 phr water. ("phr" means parts by weight per 100 parts epoxy resin by weight.) The ratio of water to epoxy resin is preferably no more than 8 phr, and more preferably no more than 5 phr.

The pressure of the reaction is not critical as long as the reagents remain in contact with each other. The pressure is preferably at least about the vapor pressure of water at the reaction temperature, in order to keep water in the reaction mixture. At preferred reaction conditions, the pressure is preferably at least 24 psig (260 kPa) and more preferably at least 85 psig (680 kPa). The pressure is preferably no more than 1000 psig (7 MPa), and more preferably no more than 250 psig (1.8 MPa). The atmosphere is not critical, as long as it does not substantially interfere with the reaction. It is preferably an inert atmosphere, such as nitrogen, helium, or argon, although air may also be used or non-condensable gases may be excluded from the reactor.

The reaction time is not critical as long as the reaction is allowed to proceed until the desired level of α-glycol is produced. The optimum time may vary depending upon the reaction conditions, the quantity of α-glycol in the starting liquid epoxy resin, and the desired quantity in the finished product. Under preferred conditions, the reaction or residence time is at least 0.5 hours, more preferably at least 1 hour, and most preferably at least 2 hours; the reaction or residence time is preferably no more than 8 hours, more preferably no more than 6 hours, and most preferably no more than 4 hours. The reaction is preferably not run beyond 8 hours, in order to limit formation of bis-α-glycol resin.

The reaction is run essentially without hydrolysis catalysts or solvents. This means that significant quantities of catalyst and solvent should not be added to the reaction mixture intentionally. Hydrolysis catalysts that should not be added include organic acids and diacids, phosphonium compounds, and alkali or alkaline earth metals or their salts. Common solvents that should not be added include aromatic and polar organic solvents, as previously described. Acceptable quantities of these impurities are described previously.

After the reaction is complete, unreacted water is preferably removed by ordinary techniques, such as by flash distillation and/or by air-drying or stripping. Flash distillation preferably occurs at about reaction temperatures under atmospheric or subatmospheric pressures. Thereafter, the resin is preferably cooled to less than 80° C. before it is stored.

The finished resin preferably contains at least 1 weight percent mono-α-glycol species, more preferably at least 2 weight percent mono-α-glycol species, and most preferably at least 4 weight percent mono-α-glycol species. It preferably contained no more than 8 weight percent mono-α-glycol species, more preferably no more than 7 weight percent mono-a-glycol species and most preferably no more than 6 weight percent mono-α-glycol species. The ratio of α-glycol moieties to glycidyl ether moieties is preferably at least 0.5 equivalent percent, more preferably at least 1 equivalent percent and most preferably at least 2 equivalent percent. The ratio is preferably no more than 4 equivalent percent, more preferably no more than 3.5 equivalent percent and most preferably no more than 3 equivalent percent.

The reaction preferably increases the quantity of mono-α-glycol species in the resin by at least 1 weight percent, more preferably at least 2 weight percent and most preferably at least 4 weight percent. It preferably increases the quantity of mono-α-glycol species in the liquid epoxy resin by no more than 8 weight percent, and more preferably no more than 6 weight percent. The reaction preferably increases the ratio of α-glycol to glycidyl ether moieties in the resin by at least 0.5 equivalent percent, more preferably at least 1 equivalent percent and most preferably at least 2 equivalent percent. It preferably increases the ratio of α-glycol to glycidyl ether moieties in the resin by no more than 4 equivalent percent, and more preferably no more than 3 equivalent percent.

An added advantage of the present invention is that the quantities of bis-α-glycol resin produced are minimized under preferred conditions. The finished resin preferably contains no more than 1 weight percent bis-α-glycol resin, more preferably no more than 0.5 weight percent, and most preferably no more than 0.1 weight percent.

The finished resin can be used for any ordinary purpose that epoxy resins are used, such as adhesives, coatings, and matrix resins in matrix composites.

WORKING EXAMPLES

The following examples are for illustrative purposes only, and are not intended to limit the scope of the claims. Unless otherwise stated, all parts and percentages are by weight.

EXAMPLE 1

A 2 L agitated pressure reactor was charged with 1000 g of liquid epoxy resin containing about 80.28 percent diglycidyl ether of bisphenol A and about 0.4 percent mono-α-glycol of the diglycidyl ether of bisphenol A. The remainder of the liquid epoxy resin was oligomers of the diglycidyl ether of bisphenol A (except for trace impurities). The reactor was purged with nitrogen to exclude air and heated to 180° C. 50 g of deionized water was added to the reactor, taking care to avoid the introduction of air. The reactor was cooled to 172° C. and the reaction was continued at 172° C. with agitation for 30 minutes. A sample of the reaction product was withdrawn and analyzed by high-performance liquid chromatography (HPLC) using a DUPONT ZORBAX ODS TM column, a 254 nm fixed wavelength UV detector and a mixture of acetonitrile and water as the eluent. It was found to contain 78.95 weight percent diglycidyl ether of bisphenol A and 1.72 weight percent mono-α-glycol of the diglycidyl ether of bisphenol A.

EXAMPLE 2

The process of Example 1 was repeated, except that the reactor was cooled to 171° C. during the reaction and the reaction was continued for 60 minutes. The analyzed sample was found to contain 77.81 weight percent diglycidyl ether of bisphenol A and 3.06 weight percent mono-α-glycol of the diglycidyl ether of bisphenol A.

EXAMPLE 3

The reaction in Example 1 was repeated except that the reaction temperature was 169° C. at the reaction was continued for 120 minutes. The analyzed sample was found to contain 75.64 weight percent diglycidyl ether of bisphenol A and 5.52 weight percent mono-α-glycol of the diglycidyl ether of bisphenol A.

EXAMPLE 4

The reaction of Example 3 was repeated. The analyzed sample was found to contain 74.78 weight percent diglycidyl ether of bisphenol A and 4.88 weight percent mono-α-glycol of the diglycidyl ether of bisphenol A.

What is claimed is:

1. A process in which a mixture that contains liquid epoxy resin and water is reacted at elevated temperatures in order to hydrolyze epoxy groups into α-glycol groups, characterized in that:

(1) the reaction temperature is between 130° C. and 200° C.;

(2) the reaction mixture contains between 0.5 and 10 parts water per 100 parts resin by weight; and (3) the mixture contains 0 to 1 weight percent organic solvents and 0 to 100 ppm each of: organic acids, organic diacids, phosphonium compounds, and alkali or alkaline earth metals and their salts, said percentages being based upon the weight of liquid epoxy resin.

2. The process of claim 1 wherein the liquid epoxy resin contains no more than 2 weight percent mono-α-glycol resin at the commencement of the reaction.

3. The process of claim 1 wherein the reaction mixture contains 2 to 8 parts water to 100 parts resin, by weight.

4. The process of claim 1 wherein the liquid epoxy resin contains 70 to 100 parts diglycidyl ether of bisphenol A, 0 to 30 parts oligomer, which are formed by the reaction of dihydric phenol with epihalohydrin, and 0 to 2 parts mono-α-glycol resin, by weight, at the commencement of the reaction.

5. The process of claim 1 wherein the reaction mixture contains less than 50 ppm each of epihalohydrins, acids, and alkali and alkaline earth metals and their salts.

6. The process of claim 1 wherein the reaction mixture contains less than 0.5 weight percent aromatic and polar organic solvents.

7. The process of claim 1 wherein the temperature of the process is 145° C. to 180° C., the pressure 680 kPa to 1.8 MPa, and the reaction time or residence time is 0.5 hours to 8 hours.

8. The process of claim 1 wherein the reaction mixture contains 2 to 5 parts water per 100 parts resin by weight.

* * * * *